United States Patent [19]

Fletcher et al.

[11] 3,937,212

[45] Feb. 10, 1976

[54] MINIATURE MUSCLE DISPLACEMENT TRANSDUCER

[76] Inventors: James C. Fletcher, Administrator of the National Aeronautics and Space Administration, with respect to an invention of Cyril Feldstein, Sierra Madre, Calif.; Jules V. Osher, Los Angeles, Calif.; Gilbert W. Lewis, Arcadia, Calif.; Robert H. Silver, Van Nuys, Calif.; Edward N. Duran, Costa Mesa, Calif.

[22] Filed: Dec. 27, 1974

[21] Appl. No.: 536,761

[52] U.S. Cl. ............ 128/2 S; 33/125 R; 33/174 D; 73/88.5 SD
[51] Int. Cl.² ........................................ A61B 5/00
[58] Field of Search ............... 128/2 R, 2 S, 2.05 P; 73/88.5 SD, 89, 93, 95, 141 R, 143, 379, 361; 33/DIG. 13, 125 B, 125 R, 174 D

[56] References Cited
UNITED STATES PATENTS

| 964,745 | 7/1910 | Blakoe | 73/381 |
|---|---|---|---|
| 2,414,161 | 1/1947 | Moore | 33/DIG. 13 |
| 2,458,354 | 1/1949 | De Forest | 33/DIG. 13 |
| 2,569,949 | 10/1951 | Prescott | 33/DIG. 13 |
| 2,924,220 | 2/1960 | Von Migsky | 128/361 |
| 2,974,527 | 3/1961 | Linthout | 73/381 |
| 3,102,420 | 9/1963 | Mason | 73/88.5 SD |
| 3,154,067 | 10/1964 | Stenstrom et al. | 128/2.05 P |
| 3,853,000 | 12/1974 | Barnett et al. | 33/DIG. 13 |
| 3,853,118 | 12/1974 | Schendel | 128/2 S |

*Primary Examiner*—William E. Kamm
*Attorney, Agent, or Firm*—John R. Manning; Monte F. Mott; Wilfred Grifka

[57] ABSTRACT

A miniature transducer for sensing muscle displacement substantially consists of a curved beam of high elastic compliance connected at its ends to two prongs. The prongs have sharpened tips which are insertable into the muscle under observation. A sensitive strain gauge is bonded to the beam preferably at the point of greatest curvature. The strain gauge output is directly related to changes in the beam curvature. As the muscle under observation expands the spacing between the prongs increases which decreases the beam curvature. On the other hand, when the muscle contracts the prongs' spacing decreases, thereby increasing the beam curvature.

7 Claims, 5 Drawing Figures

MINIATURE MUSCLE DISPLACEMENT TRANSDUCER

ORIGIN OF INVENTION

The invention described herein was made in the performance of work under a NASA contract and is subject to the provisions of Section 305 of the National Aeronautics and Space Act of 1958, Public Law 85-568 (72 Stat. 435; 42 USC 2457).

BACKGROUND OF THE INVENTION

1. Field of the Invention

The present invention generally relates to a displacement transducer and, more particularly, to a miniature transducer finding particular application in measuring muscle displacement.

2. Description of the Prior Art

Heretofore muscle displacements have been measured by employing a transducer consisting of an elastic tube, filled with a conductive fluid. The resistance across the tube changes with changes in the tube length. Mercury is one type of fluid which is often employed. One of the primary disadvantages of such a transducer is that it has to be installed while the tube is in tension, thus requiring the suturing of the tube's ends to the muscle, whose displacement is to be measured. The suturing requirement is most undesirable since it is time consuming and, more importantly, may traumatize the subject. For example, to measure the displacements of the myocardium (muscle of the heart) of an animal, used in medical research, the tube must be sutured to the myocardium while the animal is anesthetized. Other disadvantages of the prior art transducer are its inability to respond well to very small displacements, nor to displacement changes of short durations, due to its relatively large cross-sectional area and mass. Thus, a need exists for a new transducer for measuring muscle displacements, which does not have the disadvantages of the prior art transducers used for the same purpose.

OBJECTS AND SUMMARY OF THE INVENTION

It is a primary object of the present invention to provide a new miniature transducer for measuring muscle displacement.

Another object of the present invention is to provide a new miniature transducer which eliminates the need for suturing it to the muscle whose displacement is to be measured.

further object of the invention is to provide a new miniature transducer with which muscle displacements of an animal can be measured without subjecting the animal to the likelihood of a traumatization.

These and other objects of the invention are achieved by providing a transducer consisting of a thin curved beam, characterized by a high degree of elastic compliance, with two prongs attached to the beam's opposite ends. The prongs have sharp tips which are insertable into the muscle under study with minimum traumatization. Due to the high elastic compliance of the beam, it deforms in a manner very similar to the deformation or displacement of the muscle to which the beam is indirectly connected through the end prongs. A very sensitive strain gauge is attached to the curved beam between its ends, so that the smallest deformation (change in curvature) of the beam due to muscle displacement is sensed by the strain gauge which provides the electrical output, corresponding to the muscle displacement to be measured.

The novel features of the invention are set forth with particularity in the appended claims. The invention will best be understood from the following description when read in conjunction with the accompanying drawings.

DESCRIPTION OF THE PREFERRED EMBODIMENTS

Figure 1:
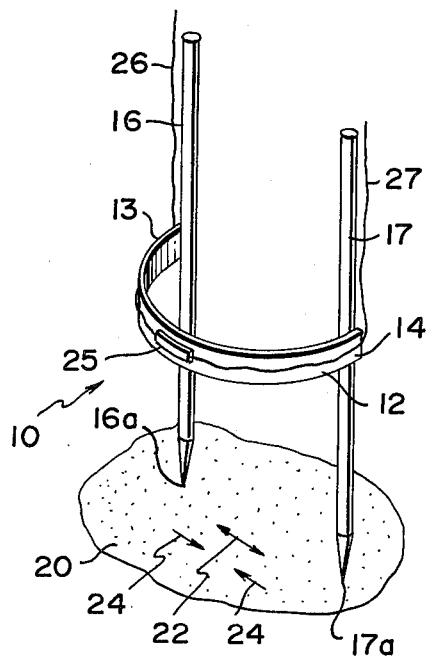
FIG. 1 is an isometric view of one embodiment actually reduced to practice.

Attention is first directed to FIG. 1 which is an isometric view of one embodiment of the invention, represented by a miniature transducer 10. The transducer consists of a very thin curved beam 12, shown in this embodiment as C-shaped. The ends 13 and 14 of the beam are securely and permanently attached to two prongs 16 and 17, with sharp end tips 16a and 17a, respectively. In practice, the tips 16a and 17a are inserted in the muscle whose displacement is to be measured. In FIG. 1, numeral 20 represents such a muscle. The beam 12 is formed of a material with a very high degree of elastic compliance, so that it deforms in a very similar way to the material surrounding it. Since the prongs 16 and 17, to which the beam 12 is attached, are inserted in the muscle 20 any deformation, i.e., displacement of the muscle directly affects the deformation of the beam 12.

For example, when the muscle 20 expands as represented by arrow 22 the distance between prongs 16 and 17 increases. Consequently, the curvature of the beam 12 decreases and the beam can be thought of as being under stress from its original shape when the prongs are initially inserted into the muscle, generally under anesthesia. On the other hand, when the muscle contracts, as represented by arrows 24, the prongs 16 and 17 move closer together, thereby increasing the beam curvature which places the beam under strain. Thus, the changes in the muscle displacement are directly reflected by changes in the beam deformation or curvature.

In accordance with the present invention a very sensitive strain gauge 25 is bonded to the outer surface of the beam 12. Consequently, any change in the deformation (curvature) of the beam 12, due to muscle displacement, is sensed by the strain gauge, whose output signal is provided across its output lines 26 and 27, which are connected to an appropriate recording or monitoring device (not shown).

From the foregoing it should thus be appreciated that the transducer of the present invention is insertable into the muscle 20 by the insertion of tips 16a and 17a of prongs into the muscle without the need of any suturing. Thus, the danger of traumatizing the subject under observation is practically eliminated. Since at present strain gauges are available which are capable of sensing extremely small displacements and have very short response time the transducer of the invention is capable of measuring small displacements as well as sensing displacement changes of very short duration.

Figure 2A:
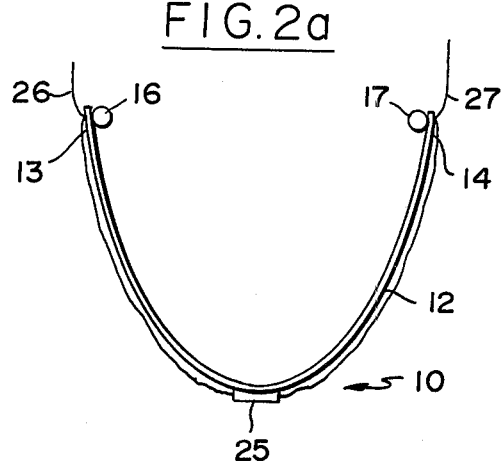
FIGS. 2a and 2b are top and side views of the embodiment shown in FIG. 1.
Figure 2B:
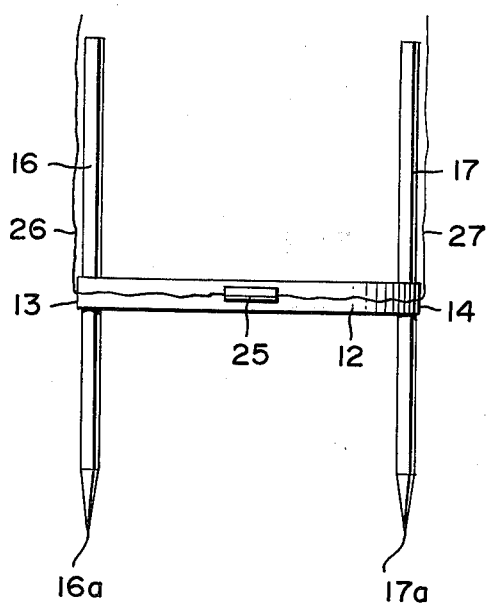

One embodiment which was actually reduced to practice, and which is presented herein for explanatory purposes, rather than to limit the invention thereto, consisted of a C-shaped beam as shown in FIGS. 1, 2a and 2b. The beam 12 was of stainless steel No. 340 several mm wide and on the order of 0.001 inch in thickness. The total beam length between ends 13 and 14 was on the order of 1 inch. The beam ends were soldered to the prongs 16 and 17 which were also of stainless steel. The beam was initially shaped (curved) so that the spacing between the prongs was on the order of 0.25 inch. Then the strain gauge 25 was bonded to the C-shaped beam at its center between ends 13 and 14, by an appropriate bonding material, e.g., epoxy. Thus, the strain gauge was attached to the beam at the surface of greatest curvature. The strain gauge may be attached on either side of the beam.

The output leads 26 and 27 of the strain gauge are preferably physically attached to the prongs 16 and 17 and therefrom are directed to the monitoring or recording device. Although various sensitive strain gauges may be used, in the embodiment actually reduced to practice, a commercially available strain gauge was used. The strain gauge was a silicon crystal of an active length of 0.05 inch and a width of 0.006 inch. It exhibited high output, extreme stability and excellent linearity. Its specification included a nominal resitance on the order of 120 ohms, with a nominal gauge factor of 120. Its temperature coefficient of resistance (TCR) is 4%/100°F. The transducer with this strain gauge was used successfully to measure deflections as small as 0.01 cm with a frequency response greater than 10 Hz.

Figure 3:
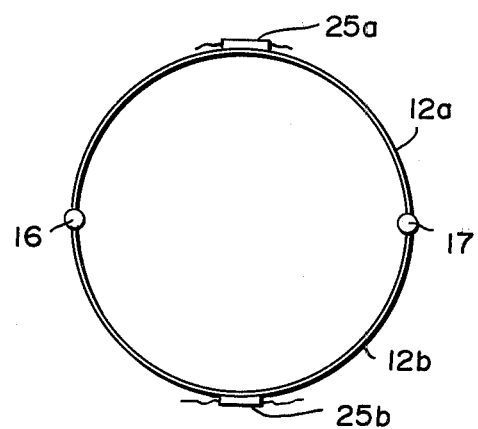
FIGS. 3 and 4 are top views of two other embodiments in accordance with the present invention.
Figure 4:
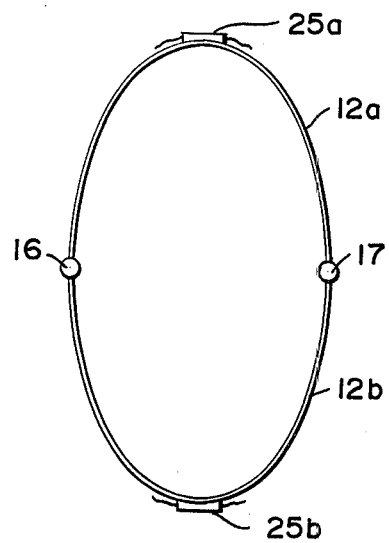

Although the transducer with the C-shaped beam was found to operate successfully, the invention is not intended to be limited thereto. As shown in FIGS. 3 and 4 the beam may be circularly shaped or oval shaped, both of which are hereinafter referred to as O-shaped. Such an O-shaped beam can be thought of as consisting of two curved beams at 12a and 12b, which are positioned on opposite sides with respect to prongs 16 and 17 to which they are attached. Each of the beams may be used to support a different strain gauge, such as strain gauge 25a on beam 12a and strain gauge 35b on beam 12b. The outputs of the two gauges can then be monitored separately for comparison or averaging purposes or connected in series to provide a greater output. However, the output of each strain gauge is sufficiently high so that such series connection may not be necessary. Clearly, if desired only one strain gauge may be employed on either of the beams.

One of the major advantages of the O-shaped beam is that it is less prone to twist. By using thinner beams the elastic compliance of the O-shaped beam may be made equal to that of the C-shaped beam.

In summary, in accordance with the present invention the miniature transducer for measuring muscle displacement comprises a curved beam having a high degree of compliance. The beam is indirectly connected to the muscle by means of prongs insertable into the muscle. As the muscle expands or contracts, i.e., undergoes displacement, the beam deforms, i.e., its curvature changes, thereby affecting a sensitive strain gauge which is attached to the deformable beam, and which provides an output signal corresponding to the muscle displacement. In practice after a transducer is fabricated it is calibrated to determine the characteristics of its output signal changes as a function of muscle displacement changes.

In use, the transducer is inserted into the muscle which contracts and expands. Thus, the resulting output signal is a cyclic signal used to indicate any irregularities in the muscle displacement.

Although the invention has been described in connection with prongs with sharpened tips 16a and 17a used to attach the transducer to the muscle, it should be appreciated that other attaching means may be employed. For example, suction cups may be attached to the ends of the prongs 16 and 17 for attaching the transducer to the muscle. Furthermore, the transducer due to its small size and the incorporation of the curved beam which supports the strain gauge can be used for other than muscle displacement measurements. For example, it may be made small enough for attachment to teeth to trace chewing movements, or to fingers of a patient to measure or trace arthritic pinch and grasp conditions. Also larger size transducers may be fabricated to measure movements (displacements) over larger portions of a patient's body. The novel transducer of the present application may find great use during open heart surgery to constantly monitor the heart muscle displacements during surgery.

The transducer may also be used in industrial applications. For example, it may be used to determine motion of moving parts in close proximity, by attaching each prong to each moving part. Due to the elastic compliance of the beam its load on the moving parts is practically insignificant. The novel transducer may also be used to detect eccentric movement between moving parts since such movement may increase or decrease the distance between the prongs attached to the two parts. It should further be stressed that the curved beam in which the strain gauge is supported is not intended to be limited to only the C-shaped or O-shaped beam which were described. For example, a spirally shaped beam may be used. Thus, in general the beam can be defined as a curved beam of high elastic compliance connected at its ends to two end prongs. A transducer is bonded to the beam at the point of greatest curvature. As the prongs' spacing changes the beam's curvature changes thereby causing a change in the output signal of the strain gauge.

Although particular embodiments of the invention have been described and illustrated herein, it is recognized that modifications and variations may readily occur to those skilled in the art and consequently, it is intended that the claims be interpreted to cover such modifications and equivalents.

What is claimed is:

1. A transducer for sensing muscle displacement comprising:
   a curved beam having first and second spaced apart ends and being of a material having a relatively high degree of elastic compliance;
   first and second elongated prongs, physically attached to the first and second ends of said beam respectively, whereby said prongs are substantially parallel to one another and are disposed in a plane which is substantially perpendicular to a plane in which said beam is disposed, said prongs having sharpened ends to facilitate the attachment of said prongs to a muscle by inserting their sharpened ends thereinto, with the beam being in a plane above said muscle; and a strain gauge in physical contact with said beam for sensing the deformation of the latter as a result of changes in the linear spacing between said substantially parallel prongs due to muscle displacement.

2. The transducer as described in claim 1 wherein said beam is substantially C-shaped with its length between its first and second ends being substantially greater than the spacing between said prongs, and said strain gauge being bonded to said beam between said first and second ends, at the point of greatest curvature between said ends.

3. The transducer as described in claim 2 wherein said beam is a rectangularly shaped narrow strip of high elastic compliance material of a thickness on the order of 0.001 inch.

4. The transducer as described in claim 3 wherein said beam is stainless steel of a thickness on the order of 0.001 inch, of a length on the order of 1 inch, said beam being curved whereby the spacing between prongs to which the beam is physically connected is on the order of 0.25 inch.

5. The transducer as described in claim 1 wherein said curved beam comprises a first curved beam unit having first and second ends respectively connected to said first and second prongs and a second curved beam unit having first and second ends respectively connected to said first and second prongs, the curved portions of said two beam units being outwardly directed from one another, so that the curved beam is O-shaped, disposed in a plane substantially perpendicular to said prongs, with the curvatures of the two units decreasing simultaneously when the linear spacing between said prongs increases, while the curvatures increase when the linear spacing between said prongs decreases, and at least one strain gauge bonded to one of said units between the ends thereof at substantially the point of greatest curvature.

6. The transducer as described in claim 5 further including a separate strain gauge bonded to each one of said curved beam units.

7. The transducer as described in claim 5 wherein each of said curved beam units consists of a rectangularly shaped thin strip of high compliance material of a thickness on the order of 0.001 inch and of a length between its ends on the order of 1 inch.

* * * * *